United States Patent
Machida et al.

(10) Patent No.: US 11,220,704 B2
(45) Date of Patent: Jan. 11, 2022

(54) METHOD FOR MEASURING HBA1C

(71) Applicant: SEKISUI MEDICAL CO., LTD., Chuo-ku (JP)

(72) Inventors: Satoshi Machida, Chuo-ku (JP); Tomohisa Nishio, Chuo-ku (JP); Kazuo Nakanishi, Chuo-ku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 163 days.

(21) Appl. No.: 16/324,414

(22) PCT Filed: Aug. 10, 2017

(86) PCT No.: PCT/JP2017/029185
§ 371 (c)(1),
(2) Date: Feb. 8, 2019

(87) PCT Pub. No.: WO2018/030531
PCT Pub. Date: Feb. 15, 2018

(65) Prior Publication Data
US 2019/0169674 A1  Jun. 6, 2019

(30) Foreign Application Priority Data
Aug. 10, 2016 (JP) .............................. JP2016-157958

(51) Int. Cl.
*C12Q 1/37* (2006.01)
*G01N 33/72* (2006.01)
*G01N 21/59* (2006.01)
*G01N 21/31* (2006.01)

(52) U.S. Cl.
CPC ............... *C12Q 1/37* (2013.01); *G01N 21/31* (2013.01); *G01N 21/59* (2013.01); *G01N 33/72* (2013.01)

(58) Field of Classification Search
CPC ..................................................... G01N 21/59
See application file for complete search history.

(56) References Cited

U.S. PATENT DOCUMENTS

| | | | |
|---|---|---|---|
| 5,449,622 A | 9/1995 | Yabe et al. | |
| 2003/0129754 A1 | 7/2003 | Samsoondar | |
| 2007/0154976 A1* | 7/2007 | Taniguchi | G01N 33/723 435/25 |
| 2007/0224685 A1 | 9/2007 | Kouzuma et al. | |

FOREIGN PATENT DOCUMENTS

| | | |
|---|---|---|
| JP | 54-116283 A | 9/1979 |
| JP | 60-35241 A | 2/1985 |
| JP | 63-50743 A | 3/1988 |
| JP | 6-241981 A | 9/1994 |
| JP | 2010-187604 A | 9/2010 |
| WO | WO 2006/013921 A1 | 2/2006 |

OTHER PUBLICATIONS

International Search Report dated Nov. 7, 2017 in PCT/JP2017/029185, citing documents AA, AB, AM-AR, AV, and AW therein, 2 pages.
Ueyama, M. et al. "Usefulness of Enzymatic HbA1c Measurement—Preparing for International HbA1c Measurement Standardization—" The Journal of the Japan Diabetic Society, vol. 53, 2010, pp. 385-389 (with English abstract).
Yonekubo, I. et al. "The trial of to avoid effects of chyle and hemolysate in analyses of biochemical items" The Japanese Journal of Medical Technology, vol. 46, 1997, pp. 1734-1738.
Hoelzel, W. et al. "IFCC Reference System for Measurement of Hemoglobin $A_{1c}$ in Human Blood and the National Standardization Schemes in the United States, Japan, and Sweden: A Method-Comparison Study" Clinical Chemistry, vol. 50, No. 1, 2004, pp. 166-174.
Extended European Search Report dated Feb. 27, 2020, in Patent Application No. 17839595.0, citing documents AA and AX-AY therein, 9 pages.
Heller, C. et al., "Lipid Interference in the Determination of the Concentration of Haemoglobin in Plasma Using the AC A SX Analyzer 1", Eur J Clin Chem Clin Biochem, Jan. 1, 1996, XP55668604, pp. 811-816.
Michels, R. et al., "Optical properties of fat emulsions", Optics Express, XP055398614, vol. 26, No. 36, Apr. 11, 2008, pp. 1571-1573.

* cited by examiner

*Primary Examiner* — Bin Shen
(74) *Attorney, Agent, or Firm* — Oblon, McClelland, Maier & Neustadt, L.L.P.

(57) ABSTRACT

Provided is a method of avoiding the influence of a coexisting substance in the measurement of HbA1c % for a whole blood sample by an enzymatic method. Specifically, provided is a method of measuring a ratio of a hemoglobin A1c concentration to a hemoglobin concentration in a sample by an enzymatic method, the method including: a first step of optically measuring the hemoglobin concentration; and a second step of optically measuring the hemoglobin A1c concentration, wherein, when HbA1c % is calculated by dividing the hemoglobin A1c concentration measured in the second step by the hemoglobin concentration measured in the first step, the hemoglobin concentration serving as a denominator, which is measured at a first wavelength, is corrected using a result measured at a second wavelength.

1 Claim, 6 Drawing Sheets

[Fig. 6]
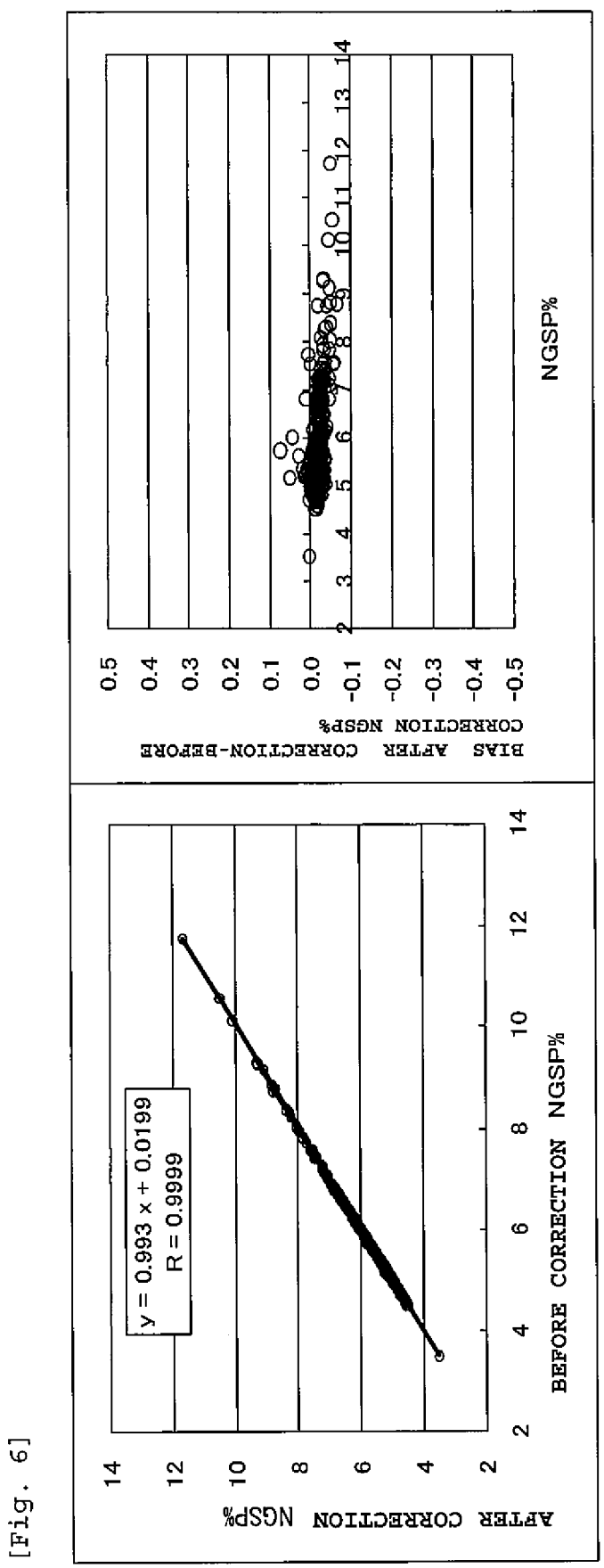

METHOD FOR MEASURING HBA1C

FIELD OF THE INVENTION

The present invention relates to a method of measuring HbA1c. Specifically, the present invention relates to a method of measuring HbA1c using an automated analyzer.

BACKGROUND GROUND OF THE INVENTION

Hemoglobin A1c (HbA1c) is formed through glycation of an N-terminus of a β-chain of $HbA_0$, and is a glycation product of $HbA_0$, which accounts for most hemoglobin. A presence ratio of HbA1c to a total hemoglobin amount reflects an average blood sugar level in 1 month to 2 months before blood collection from an individual to be tested, and hence is widely utilized as an indicator of a glycemic control state in diabetes, for clinical diagnosis or therapy selection.

The presence ratio of HbA1c is calculated as a ratio (%) of a hemoglobin A1c concentration (μmol/L) to a hemoglobin concentration (μmol/L) in the case of NGSP %, or as a ratio (mmol/mol) of hemoglobin A1c (mmol) to 1 mol of hemoglobin in the case of an IFCC value. The calculated presence ratio of HbA1c is hereinafter sometimes generically referred to as HbA1c %. As a method of measuring HbA1c for calculating the HbA1c %, there have been reported an HPLC method, an immunoagglutination method, an electrophoresis method, and an enzymatic method. Of those, the enzymatic method is a method put into practical use in recent years, is applicable to an automated analyzer frequently used in the field of clinical examination, and has an advantage of less contamination of the automated analyzer (in particular, a reaction cell) with a reagent as compared to the immunoagglutination method, which is also applicable to the automated analyzer.

Blood cells separated from whole blood are used as a sample for measurement of the HbA1c % in some cases, and whole blood is used as the sample in other cases. However, with regard to the enzymatic method, although there is a report on a case in which whole blood is used as the sample, technological accumulation is still insufficient.

CITATION LIST

Non Patent Literature

[NPL 1] Clin. Chem., 50(1), 166-174 (2004)

SUMMARY OF THE INVENTION

Technical Problem

The inventors of the present invention had the following experience while making investigations on a case in which whole blood was used as a sample in an enzymatic method: an error sometimes occurred under a strong influence of a coexisting substance in the sample. The present invention was made in view of the above-mentioned circumstances, and an object of the present invention is to provide a method of avoiding the influence of a coexisting substance in the measurement of HbA1c % by an enzymatic method using whole blood as a sample.

Solution to the Problem

According to one embodiment of the present invention, there is provided a method of measuring a ratio (HbA1c %) of a hemoglobin A1c concentration to a hemoglobin concentration in a sample by an enzymatic method, the method comprising: a first step of optically measuring the hemoglobin concentration; and a second step of optically measuring the hemoglobin A1c concentration, wherein, when HbA1c % is calculated by dividing the hemoglobin A1c concentration measured in the second step by the hemoglobin concentration measured in the first step, the hemoglobin concentration serving as a denominator, which is measured at a first wavelength, is corrected using a result measured at a second wavelength that satisfies the following conditions: a longer wavelength than 480 nm; a wavelength that gives an absorbance equal to or less than 1/10 of an absorbance at 480 nm for a 100 μmol/L solution of hemoglobin in physiological saline; and a wavelength at which a correlation exists between a fat particle concentration and an absorbance.

According to one embodiment of the present invention, there is provided a method of measuring a ratio (HbA1c %) of a hemoglobin A1c concentration to a hemoglobin concentration in a sample by an enzymatic method, the method comprising: a first step of optically measuring the hemoglobin concentration; and a second step of optically measuring the hemoglobin A1c concentration, wherein, when HbA1c % is calculated by dividing the hemoglobin A1c concentration measured in the second step by the hemoglobin concentration measured in the first step, the hemoglobin concentration serving as a denominator, which is measured by a first wavelength selected from 450 nm to 610 nm, is corrected using a result measured at a second wavelength selected from 690 nm to 900 nm.

According to one embodiment of the present invention, there is provided a method of measuring a ratio (HbA1c %) of a hemoglobin A1c concentration to a hemoglobin concentration in a sample by an enzymatic method, the hemoglobin concentration being optically measured in a first step, the hemoglobin A1c concentration being optically measured in a second step, wherein, when HbA1c % is calculated by dividing the hemoglobin A1c concentration measured in the second step by the hemoglobin concentration measured in the first step, the hemoglobin concentration serving as a denominator, which is measured at a first wavelength selected from 450 nm to 610 nm, is, corrected using concentration information on lipid particles and concentration information on hemoglobin that are measured at a second wavelength selected from 690 nm to 900 nm.

Advantageous Effects of the Invention

According to the present invention, an error resulting from a sample-derived dye (e.g., turbidness due to chyle) can be corrected in the method of measuring HbA1c for a whole blood sample using an automated analyzer. In addition, according to the present invention, in the measurement of the HbA1c % by the enzymatic method using whole blood as a sample, the influence of the coexisting substance in the sample can be avoided on the automated analyzer side without changing the composition of a reagent. According to the present invention, in the measurement of the HbA1c % by the enzymatic method using whole blood as a sample, accurate measurement of the HbA1c % can be easily performed even for a special specimen (e.g., a chyle specimen).

BRIEF DESCRIPTION OF THE DRAWINGS

FIG. 6 is graphs for showing a relationship between a case without hemoglobin concentration correction and a case with correction for HbA1c % measured values according to a method of the present invention using actual specimens. In the left graph, the X-axis represents HbA1c % before correction and the Y-axis represents HbA1c % after correction, and in the right graph, the X-axis represents HbA1c % after correction and the Y-axis represents the bias of HbA1c % with correction with respect to HbA1c % without correction (with correction-without correction).

DESCRIPTION OF PREFERRED EMBODIMENTS

Figure 1:
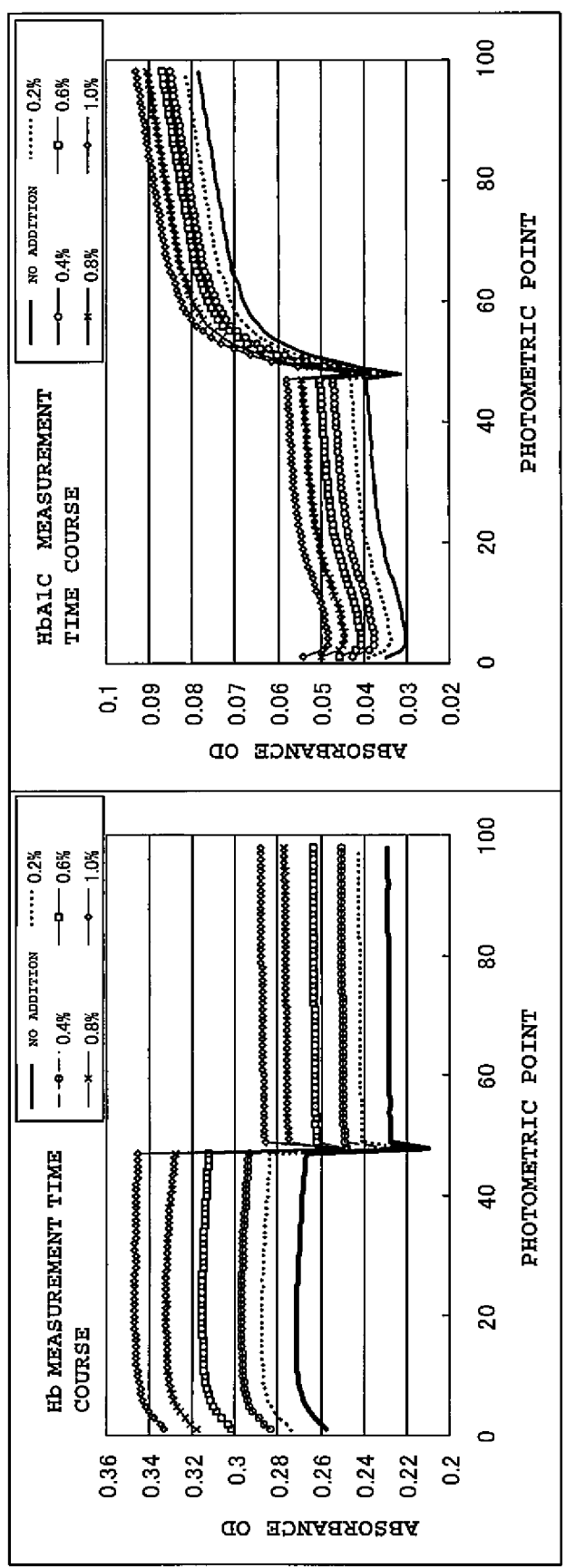
FIG. 1 is graphs for showing a reaction time course in hemoglobin concentration measurement (left graph) and a reaction time course in hemoglobin A1c concentration measurement (right graph) in the case where Intralipid-containing samples are subjected to measurement by an enzymatic method.

A method of measuring HbA1c % based on an enzymatic method using an automated analyzer mainly comprises: a first step of optically measuring hemoglobin; a second step of optically measuring HbA1c; and an operation step of dividing a value measured in the second step by a value measured in the first step. When this measurement method is carried out with a whole blood sample, a measurement error due to the influence of a coexisting substance, such as chyle, in blood may occur. The inventors of the present invention provide a method of measuring HbA1c % capable of correcting the measurement error.

Now, the present invention is described by exemplifying preferred embodiments of the present invention.

First Embodiment

A method of measuring a ratio (HbA1c %) of a hemoglobin A1c concentration to a hemoglobin concentration in a sample by an enzymatic method, the method comprising: a first step of optically measuring the hemoglobin concentration; and a second step of optically measuring the hemoglobin A1c concentration, wherein, when HbA1c % is calculated by dividing the hemoglobin A1c concentration measured in the second step by the hemoglobin concentration measured in the first step, the hemoglobin concentration serving as a denominator, which is measured at a first wavelength, is corrected using a result measured at a second wavelength that satisfies the following conditions: a longer wavelength than 480 nm; a wavelength that gives an absorbance equal to or less than 1/10 of an absorbance at 480 nm for a 100 µmol/L solution of hemoglobin in physiological saline; and a wavelength at which a correlation exists between a fat particle concentration and an absorbance.

Second Embodiment

A method of measuring a ratio (HbA1c %) of a hemoglobin A1c concentration to a hemoglobin concentration in a sample by an enzymatic method, the method comprising: a first step of optically measuring the hemoglobin concentration; and a second step of optically measuring the hemoglobin A1c concentration, wherein, when HbA1c % is calculated by dividing the hemoglobin A1c concentration measured in the second step by the hemoglobin concentration measured in the first step, the hemoglobin concentration serving as a denominator, which is measured by a first wavelength selected from from 450 nm to 610 nm, is corrected using a result measured at a second wavelength selected from 690 nm to 900 nm.

Third Embodiment

A method of measuring a ratio (HbA1c %) of a hemoglobin A1c concentration to a hemoglobin concentration in a sample by an enzymatic method, the hemoglobin concentration being optically measured in a first step, the hemoglobin A1c concentration being optically measured in a second step, wherein, when HbA1c % is calculated by dividing the hemoglobin A1c concentration measured in the second step by the hemoglobin concentration measured in the first step, the hemoglobin concentration serving as a denominator, which is measured at a first wavelength selected from 450 nm to 610 nm, is corrected using concentration information on lipid particles and concentration information on hemoglobin that are measured at a second wavelength selected from 690 nm to 900 nm.

The method of measuring HbA1c % according to the present invention basically comprises: a first step of optically measuring a hemoglobin concentration in a sample; a second step of optically measuring an HbA1c concentration in the sample; and a step of calculating a ratio (HbA1c %) of the HbA1c concentration to the hemoglobin concentration in the sample. In the first step, the optical measurement of the sample is performed by measuring an absorbance through the use of each of light having a first wavelength and light having a second wavelength. The hemoglobin concentration measured at the first wavelength is corrected using the measured value at the second wavelength. The corrected hemoglobin concentration is used in the HbA1c % calculation step. That is, in the HbA1c % calculation step, the HbA1c % is calculated by dividing the HbA1c concentration measured in the second step by the corrected hemoglobin concentration. In the method of measuring HbA1c % of the present invention, through the use of the corrected hemoglobin concentration as the hemoglobin concentration serving as the denominator, a measurement error resulting from a coexisting substance, such as chyle, in the sample is corrected, and thus the HbA1c % is measured with high accuracy.

Many of automated analyzers do not have a mechanism for avoiding the influence of the coexisting substance (such as chyle) in the sample in the measurement of the hemoglobin concentration in the first step. Meanwhile, when the method of the present invention is applied to any of various automated analyzers, there can be provided a method of measuring HbA1c % in which the influence of the coexisting substance is eliminated.

Examples of the "sample" or "specimen" to be used in the method of the present invention include: whole blood; red blood cells separated from whole blood; and red blood cells separated from whole blood and further washed. The method of the present invention can avoid the influence of the coexisting substance (such as chyle) in blood, and hence allows the use of whole blood as the sample without any problem.

As used herein, the term "chyle specimen" refers to a specimen (such as serum) exhibiting a milky white color because of fat particles contained therein. Most of fats ingested as a meal are neutral fats, and after being absorbed into blood, are decomposed by an enzyme, such as lipoprotein lipase, and metabolized into fatty acids or the like. When blood is collected immediately after a meal, the fats remain in the blood without being well decomposed, and the fat content looks white, and hence the specimen looks cloudy. The cloudiness is remarkable in a specimen collected from an individual with an abnormality in lipid metabolism, irrespective of the timing of the meal. The neutral fats in the blood include ones that have been absorbed from the meal into the blood (mainly chylomicrons) and ones that have been synthesized in the liver (mainly VLDL). The cloudiness of the chyle specimen is mostly caused by the chylomicrons, which transiently increase after a meal.

As used herein, the term "fat particles" only needs to have a general meaning in the field of clinical examination or the like, but preferably refers to particles constituted of the fat content contained in the chyle specimen (e.g., chylomicrons or VLDL). Alternatively, a soybean-derived lipid (such as lecithin) contained in a lipid emulsion (e.g., Intralipid or Intralipos) to be added to an infusion for supplying energy to a patient in a clinical setting may also be included in the fat particles herein.

The optical measurement of the HbA1c concentration in the second step of the method of the present invention may be basically carried out in accordance with a general method that has heretofore been performed with an automated analyzer. The second step is performed using a so-called coloring agent, and hence the coloring agent to be used determines the wavelength in the optical measurement. The second step is carried out in the co-presence of hemoglobin, and hence is preferably performed on a longer wavelength side than 480 nm, which hardly overlaps the absorption wavelength of hemoglobin. A suitable example of the wavelength may be a wavelength of from 550 nm to 750 nm.

As used herein, the term "HbA1c %" means a ratio (%) between a hemoglobin A1c concentration and a hemoglobin concentration in a sample, which is generally used in a clinical setting. Examples of the HbA1c % include: a value specified as a National Glycohemoglobin Standardization Program (NGSP) value: a value specified as an International Federation of Clinical Chemistry and Laboratory Medicine (IFCC) value; and a value specified as a Japan Diabetes Society (JDS) value. Unless otherwise stated, the term "HbA1c %" as used herein generically means those values (see Non Patent Literature 1 for an interrelationship between the individual values). The calculation of the HbA1c % in the method of the present invention may be performed in accordance with the standard of NGSP, IFCC, JDS, or the like.

The enzymatic method to which the present invention is applicable is not particularly limited, and a known method may be used. As an example of the enzymatic method that is preferred as a highly specific measurement method, there is given a method involving: digesting and cleaving a glycated dipeptide at the N-terminus of a β-chain of HbA1c with a protease in a first reaction, and simultaneously, determining a hemoglobin concentration at a predetermined wavelength; and allowing a specific oxidase to act on the glycated dipeptide in a second reaction, and subjecting the generated hydrogen peroxide to coloring with a coloring agent in the presence of a peroxidase, followed by colorimetric determination. Reagents for HbA1c % measurement based on the enzymatic method are marketed as in vitro diagnostics, and such reagents may be used. In addition, in the enzymatic method to be used in the present invention, various modifications and alterations in enzymatic methods that have already been reported may also be appropriately adopted.

In the measurement of the hemoglobin concentration, treatment for stabilizing an absorbance may be performed by causing hemoglobin to have a constant structure by a known method, such as conversion to methemoglobin. In addition, in the measurement of the HbA1c concentration, treatment for facilitating the digestion and cleavage of the glycated dipeptide from the β-chain of HbA1c may be performed by allowing a surfactant or the like to be co-present at the time of the digestion and cleavage with the protease.

As used herein, the term "first wavelength" means a wavelength for measuring hemoglobin, and preferably refers to a first light wavelength to be used for the optical measurement of the hemoglobin concentration in the first step of the method of the present invention. The first wavelength may be appropriately selected from the range of from 450 nm to 610 nm.

As used herein, the term "second wavelength" means a wavelength for correcting an apparent hemoglobin concentration measured at the first wavelength to a true hemoglobin concentration, and preferably refers to a second light wavelength to be used for the optical measurement in the first step of the method of the present invention. The second wavelength may be appropriately selected from the range of from 690 nm to 900 nm. From a different viewpoint, the second wavelength may be selected from wavelengths each of which is a longer wavelength than 480 nm, is a wavelength that gives an absorbance equal to or less than $^{1}\!/_{10}$ of an absorbance at 480 nm for a 100 µmol/L solution of hemoglobin in physiological saline, and is a wavelength at which a correlation exists between a fat particle concentration and an absorbance. In the method of the present invention, the measurement at the second wavelength in the first step may be performed after, prior to, or concurrently with the measurement at the first wavelength.

As used herein, the term "wavelength" in each of the terms "first wavelength" and "second wavelength" refers to a main wavelength, and does not mean a so-called "sub wavelength", at which measurement is performed for, for example, the purpose of background correction.

As used herein, the term "inter-item operation" refers to the correlating of a measured value for hemoglobin A1c and a measured value for hemoglobin each of which has been independently measured, and the operation may be performed with the operation function of the automated analyzer.

In the method of the present invention, the calculation of the corrected hemoglobin concentration only needs to be performed during a period between the acquisition of the measured values at the first and second wavelengths in the first step and the HbA1c % calculation. For example, the calculation may be performed immediately after the acquisition of the measured values at the first and second wavelengths in the first step, may be performed concurrently with the second step, or may be performed immediately before the HbA1c % calculation.

The procedure of the calculation of the corrected hemoglobin concentration according to the present invention is described. The procedure of the correction may be basically described or constructed through a test using a sample containing a lipid emulsion or an interfering substance reagent for evaluating the performance of a measurement system, the sample giving properties similar to those of the chyle specimen (specimen containing fat particles). Examples of the lipid emulsion include, but not limited to, Intralipid and Intralipos, and the reagent for evaluating the performance of a measurement system is, for example, Interference Check A, but is not limited thereto.

In the measurement of the sample at the first wavelength for measuring hemoglobin, absorption by lipid particles is added to absorption by hemoglobin, leading to a rise in absorbance of the sample as a whole. Thus, the hemoglobin concentration measured at the first wavelength has an increased value (falsely increased value) with respect to a true hemoglobin concentration.

On the basis of a difference between the hemoglobin concentration of a sample containing lipid particles (apparent hemoglobin concentration) and the hemoglobin concentration of a sample containing no lipid particles (true hemoglobin concentration), which are calculated from absorbances at the first wavelength, a false increase in hemoglobin concentration value (false increase in hemoglobin concentration value: $X_{lipid}$), in which the lipid particles are measured as hemoglobin, is determined. $X_{lipid}$ is a rising in hemoglobin concentration measured value at the first wavelength resulting from the lipid particles.

Meanwhile, a plurality of samples containing the lipid particles at different concentrations are subjected to measurement at the second wavelength, and a fluctuation in absorbance dependent on the concentration of the lipid particles is investigated to determine a relational equation (regression equation) [Equation A] between the false increase in hemoglobin concentration value ($X_{lipid}$) and the absorbance ($Y_{lipid}$) of the lipid particles at the second wavelength.

$X_{lipid}=a_1 Y_{lipid}-b_1$ ($a_1$ represents a slope and $b_1$ represents an intercept.) [Equation A]:

Through the utilization of the [Equation A], the apparent hemoglobin concentration is corrected to the true hemoglobin concentration with the following [Equation B].

Corrected hemoglobin concentration=apparent hemoglobin concentration−false increase in hemoglobin concentration value=apparent hemoglobin concentration−($a_1 Y_{lipid}-b_1$) [Equation B]:

Through the use of the corrected hemoglobin concentration, the HbA1c % may be calculated in the following manner in the case of NGSP %.

HbA1c % (NGSP %)=HbA1c concentration/corrected hemoglobin concentration*91.5+2.15

Another mode of the HbA1c % calculation method of the present invention is described.

The second wavelength is most suitably a wavelength at which absorption by hemoglobin is zero. However, owing to the problem of sensitivity, the absorption cannot substantially be made zero in some cases depending on the concentration of hemoglobin. In such cases, the influence of the hemoglobin concentration on the measured value at the second wavelength may be corrected in the following manner.

A relational equation (regression equation) [Equation C] between the hemoglobin concentration ($X_{Hb}$) of a sample and a change ($Y_{Hb}$) in absorbance of the sample at the second wavelength is determined.

$Y_{Hb}=a_2 X_{Hb}-b_2$ ($a_2$ represents a slope and $b_2$ represents an intercept.) [Equation C]:

With this relational equation, the change in absorbance at the second wavelength dependent on the hemoglobin concentration of the sample is determined.

Through the utilization of the [Equation C], an absorbance derived from the fat particle concentration from which the influence of the hemoglobin concentration at the second wavelength has been eliminated (corrected fat particle absorbance: $Y_{lipid}$ offset) is determined in the following manner.

Corrected fat particle absorbance $Y_{lipid}$ offset=absorbance of sample at second wavelength−change in absorbance dependent on hemoglobin concentration at second wavelength=absorbance of sample at second wavelength−$Y_{Hb}$ [Equation D]:

Through the use of the corrected fat particle absorbance $Y_{lipid}$ offset, the false increase in hemoglobin concentration value $X_{lipid}$ is further corrected to calculate a false increase in hemoglobin concentration value 2: $X_{lipid-2}$.

False increase in hemoglobin concentration value 2: $X_{lipid-2}$=corrected fat particle absorbance $Y_{lipid}$ offset*$a_1$=(absorbance of sample at second wavelength−$X_{Hb}$*$a_2$)*$a_1$ [Equation E]:

It is understood that the intercept $b_1$ in [Equation A] is a numerical value that fluctuates depending on the hemoglobin concentration represented by "−$X_{Hb}$*$a_2$*$a_1$" in [Equation E].

Through the use of the falsely increased hemoglobin concentration value 2: $X_{lipid-2}$, the corrected hemoglobin concentration is further corrected to calculate a corrected hemoglobin concentration 2.

Corrected hemoglobin concentration 2=apparent hemoglobin concentration−false increase in hemoglobin concentration value 2: $X_{lipid-2}$=apparent hemoglobin concentration−(absorbance of sample at second wavelength−$X_{Hb}$*$a_2$)*$a_1$ [Equation F]

Through the use of the corrected hemoglobin concentration 2, the HbA1c % may be calculated in the following manner in the case of NGSP %.

HbA1c % (NGSP %)=HbA1c concentration/corrected hemoglobin concentration 2*91.5+2.15

The present invention can be suitably used for a method involving continuously measuring hemoglobin and HbA1c in the same reaction chamber, but the first step and the second step may be performed in separate reaction chambers. A person skilled in the art would naturally understand that the present invention can also be utilized in, for example, the case where: in one chamber, only the first step is performed to measure hemoglobin; and in another chamber, the reagents of the first step are added but hemoglobin is not measured, and subsequently the second step is performed to measure HbA1c.

EXAMPLES

Now, the present invention is described in detail by way of Examples. However, the present invention is not limited to Examples.

Reference Example 1

The influence of a lipid emulsion on HbA1c % was confirmed.
1. Materials
(1) Sample: Whole blood collected with EDTA was pooled and used. This sample is hereinafter sometimes referred to as pooled whole blood.
(2) Measurement Reagents and Calibrator:
<Pretreatment Liquid>
10 mM sodium nitrite
<Protease-Containing Substrate Reagent (R1)>
50 mM of a protease-containing substrate reagent containing the following components
Sodium phosphate buffer pH 7.0
1.5% AMPHITOL 20BS (Kao Corporation)
2.0 mg/mL PROTIN PC10F (Daiwa Kasei Industry Co., Ltd.)
0.01% sodium azide (manufactured by Kishida Chemical Co., Ltd.)
50 µM DA-67 (sodium 10-(carboxymethylaminocarbonyl)-3,7-bis(dimethylamino) phenothiazine, Wako Pure Chemical Industries, Ltd.)
<Coloring Reagent (R2)>
50 mM of a coloring reagent containing the following components
Sodium phosphate buffer pH 7.0
10 U/mL fructosyl peptide oxidase (Kikkoman Corporation)
1 U/mL peroxidase (Toyobo Co., Ltd.)
<Calibrator>
NORUDIA N HbA1c calibrator (Sekisui Medical Co., Ltd.) was used.
(3) Lipid emulsion: Intralipid (Fresenius Kabi) was used.
2. Procedure
(1) Preparation of test samples: Test samples were prepared by adding Intralipid to the pooled whole blood at final concentrations in Table 1.
(2) Measurement of test samples: Through the use of an automated analyzer JCA-BM9130 (JEOL Ltd.), the test samples were subjected to measurement with the following measurement parameters, and HbA1c % was measured.

In addition, for each test sample, reaction time courses in hemoglobin concentration measurement and hemoglobin A1c concentration measurement were confirmed.
Parameters:
[HbA1c and Hb]
Analysis method: EPA
Calculation method: MSTD
Measurement wavelength (sub/main): HbA1c 805/658, Hb 805/478
Main DET.Pl-P.m-P.n: HbA1c 0-95-98, Hb 0-44-47
Sub DET.P.p-P.r: HbA1c 44-47, Hb 0-0
Reaction time: 10 min
At the time of blood cell measurement:
Diluted specimen amount (whole blood amount): 4.0 µL
Diluent amount (diluent): 110 µL
At the time of calibrator measurement:
Diluted specimen amount (calibrator): 25 µL
Diluent amount (diluent): 15 µL
Reaction specimen amount (Sample amount): 6.4 µL
First reagent amount (R1): 60 µL, second reagent amount: 0 µL,
Third reagent amount (R2): 20 µL, fourth reagent amount: 0 µL 3. Results
(1) Fluctuation of Each Measured Value
An increase in hemoglobin concentration measured value and decrease in HbA1c % dependent on the concentration of Intralipid in the test sample were confirmed. Meanwhile, the HbA1c concentration measured value was nearly constant (see Table 1 for the foregoing). In view of the foregoing, it was considered that the decrease in HbA1c % resulted from the increase in hemoglobin concentration measured value serving as the denominator in HbA1c % calculation.

TABLE 1

| Intralipid concentration (%) | Hemoglobin concentration (µmol/L) | HbA1c concentration (µmol/L) | HbA1c % (NGSP %) |
|---|---|---|---|
| 0 | 110.9 | 4.54 | 5.90 |
| 0.2 | 118.3 | 4.55 | 5.67 |
| 0.4 | 128.2 | 4.63 | 5.45 |
| 0.6 | 130.1 | 4.42 | 5.26 |
| 0.8 | 143.7 | 4.61 | 5.09 |
| 1.0 | 155.1 | 4.69 | 4.92 |

(2) Confirmation of Reaction Time Courses
The reaction time courses in the hemoglobin concentration measurement and the HbA1c concentration measurement for each test sample are shown in FIG. 1. For all test samples, increases in absorbance dependent on the concentration of Intralipid in the hemoglobin concentration measurement (left of FIG. 1) and the HbA1c concentration measurement (right of FIG. 1) were confirmed. In hemoglobin concentration measurement with a general automated analyzer like the automated analyzer JCA-BM9130 used in this Reference Example, the detected absorbance itself is used for the calculation of the hemoglobin concentration. Accordingly, it was presumed that, in this test, the increase in absorbance derived from Intralipid was directly added to the absorbance of hemoglobin, and as a result, the hemoglobin concentration measured value was falsely increased as shown in Table 1. Meanwhile, in the HbA1c concentration measurement with the automated analyzer used in this Reference Example, an absorbance subjected to correction with measured values at a main wavelength and a sub wavelength immediately before the addition of the coloring reagent is used as an absorbance to be used for the calculation of the HbA1c concentration, and hence only an increase in absorbance caused by coloring of the coloring reagent is used for the calculation of the HbA1c concentration. Accordingly, it was presumed that, in the HbA1c concentration measurement in this test, a falsely increased value like that in the hemoglobin concentration measurement was not observed.

Reference Example 2

Figure 2:
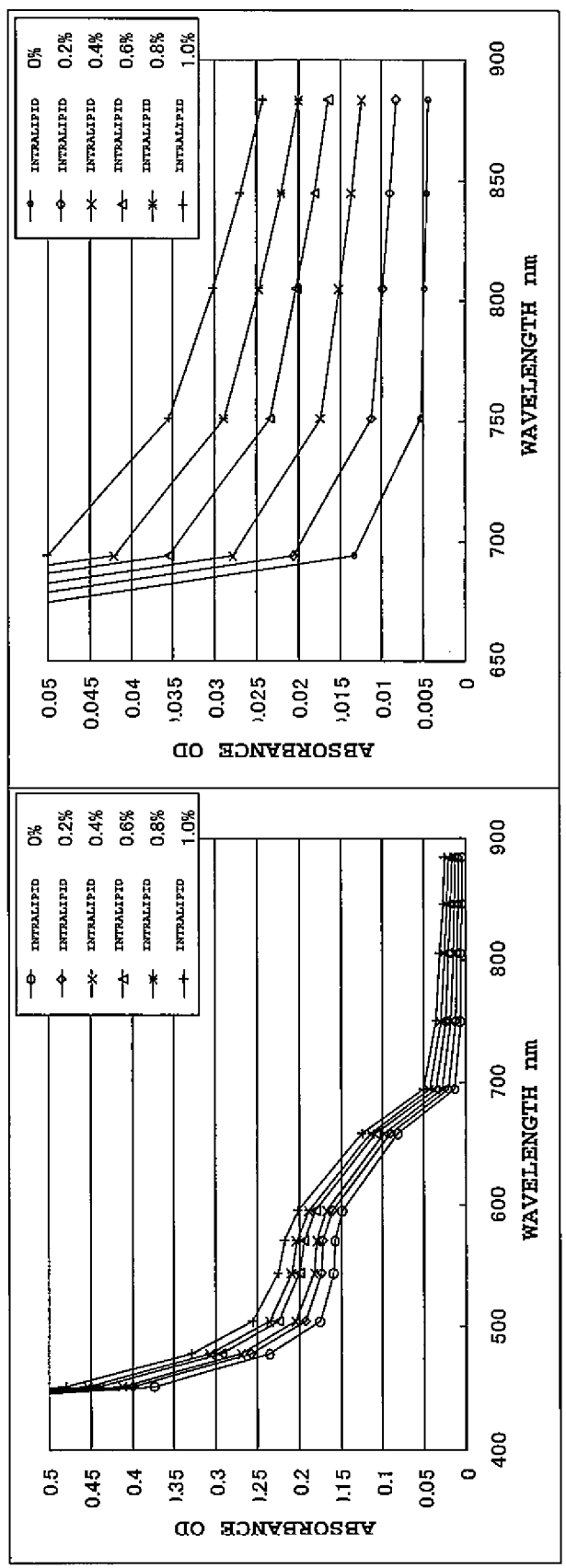
FIG. 2 is graphs for showing the absorption spectra of Intralipid-containing samples at from 400 nm to 900 nm. In the left graph, measurement results in the range of from 400 nm to 900 nm are shown, and the right graph is an enlarged graph for the range of from 650 nm to 900 nm.

As a result of absorption spectral analysis of the test samples (FIG. 2), a wavelength in the range of from about 690 nm to about 900 nm was found to be an absorption wavelength at which the absorption of hemoglobin and the coloring reagent at the time of coloring was small, and which correlated with the concentration of Intralipid. From this range, 884 nm was selected, and a correlation with a falsely increased value of the hemoglobin concentration derived from Intralipid as observed in Table 1 was confirmed.
1. Procedure
The absorbance of Intralipid at 884 nm was defined as (X), and the difference between the hemoglobin concentration measured value at 478 nm for each Intralipid concentration in Table 1 and the hemoglobin concentration measured value of the test sample with no addition of Intralipid at 884 nm was defined as a hemoglobin concentration rise due to the falsely increased value (false increase in hemoglobin concentration value: Y), and a correlation coefficient ($R^2$) and regression equation (Y=aX−b) therebetween were determined.

2. Results

Figure 3:
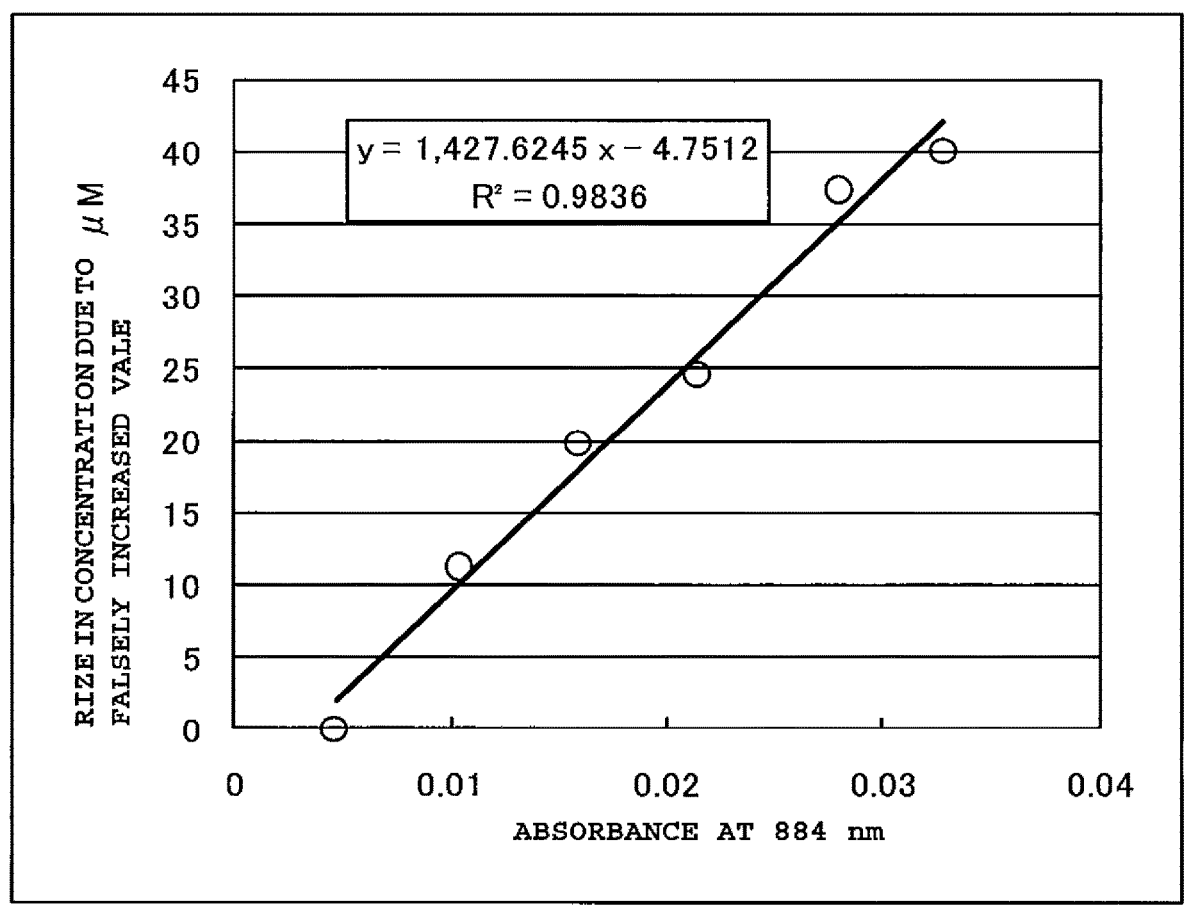
FIG. 3 is a graph for showing a relationship between the absorbance of Intralipid at a second wavelength (884 nm) and a false increase in hemoglobin concentration value.

The correlation coefficient: $R^2$=0.9836 and the regression equation: Y=1427.6X−4.7512 [Equation A1] were obtained, and thus it was confirmed that the false increase in hemoglobin concentration value resulted from Intralipid (FIG. 3).

Example 1

The correction of the hemoglobin concentration was investigated through the utilization of the regression equation of the false increase in hemoglobin concentration value obtained by the measurement at 884 nm.

1. Procedure

[Equation B1] was derived from the regression equation [Equation A1] obtained in Reference Example 2, the hemoglobin concentration measured value (apparent hemoglobin concentration) at 478 nm was corrected with [Equation B1], and HbA1c % was calculated using the hemoglobin concentration after correction.

Hemoglobin concentration after correction=apparent hemoglobin concentration−false increase in hemoglobin concentration value =apparent hemoglobin concentration−(absorbance at 884 nm*1,400−5) where 1,400 is a simplified numerical value for the slope of the regression equation, and −5 is a simplified numerical value for the intercept.   [Equation B1]

2. Results

The HbA1c % calculated with the hemoglobin concentration after correction determined by [Equation B1] approximated to the value for no addition of Intralipid, and besides, a decrease in value dependent on the concentration of Intralipid was not observed (Table 2).

TABLE 2

| Intralipid concentration (%) | HbA1c % before correction (NGSP %) | HbA1c % after correction (NGSP %) |
|---|---|---|
| 0.0 | 5.90 | 5.85 |
| 0.2 | 5.67 | 5.83 |
| 0.4 | 5.45 | 5.79 |
| 0.6 | 5.26 | 5.77 |
| 0.8 | 5.09 | 5.75 |
| 1.0 | 4.92 | 5.77 |

Thus, it was confirmed that the falsely increased value of the hemoglobin concentration due to Intralipid was able to be corrected by correcting the hemoglobin concentration using [Equation B1] derived from the absorbance at 884 nm.

Example 2

In Example 1, it was confirmed that the falsely increased value of the hemoglobin concentration due to the addition of Intralipid was able to be corrected, but the samples having added thereto Intralipid were found to have slightly decreased values of HbA1c %. This was considered to be due to the influence of the fact that the absorption of hemoglobin at 884 nm was not zero. In view of this, the influence was confirmed.

1. Materials (1) Samples: panel specimen (washed blood cells) (Sekisui Medical Co., Ltd.) 3 kinds (levels 1, 3, and 5) [HbA1c values: 5.0% (level 1); 8.0% (level 3); and 11.8% (level 5)]
(2) Pretreatment liquid: The pretreatment liquid described in Reference Example 1 was used.

2. Procedure

Each panel specimen was diluted with the pretreatment liquid 7-fold and 80-fold to prepare hemoglobin concentration-adjusted liquids, and the two liquids were appropriately mixed to prepare 11 kinds for each level of measurement samples having a constant HbA1c % and different hemoglobin concentrations. The HbA1c % of each of the measurement samples was measured using the same procedure as in Reference Example 1 except that the diluted specimen amount (blood cell amount) was set to 2.0 µL. The correction of the hemoglobin concentration was performed with [Equation B1] as in Example 1.

3. Results

Figure 4:
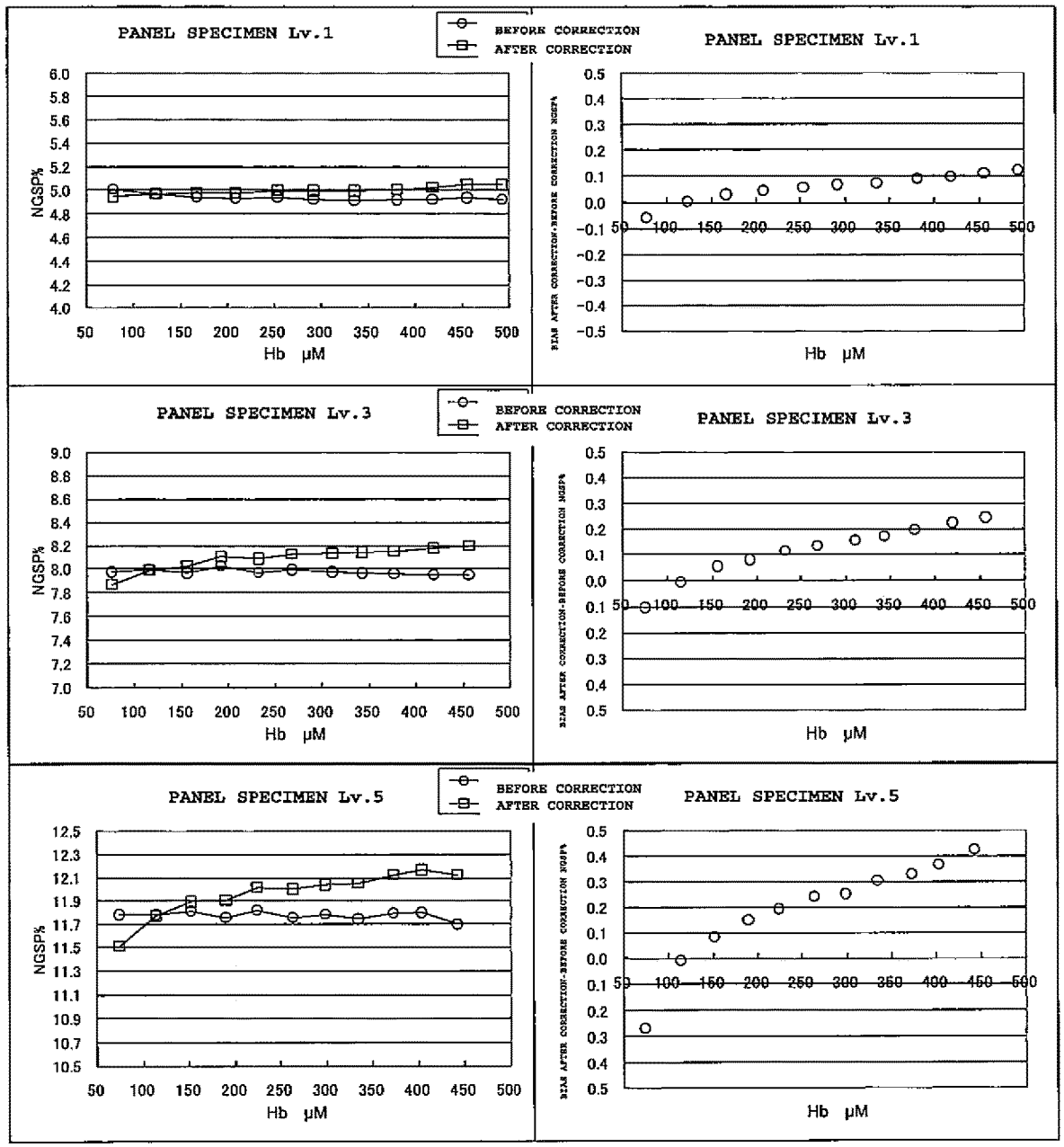
FIG. 4 is graphs for showing relationships between the hemoglobin concentration of a sample and HbA1c % measured in Example 2. In each of the left graphs, the X-axis represents a hemoglobin concentration and the Y-axis represents HbA1c % (Y-axis), and in each of the right graphs, the X-axis represents a hemoglobin concentration and the Y-axis represents the bias of HbA1c % after correction with respect to HbA1c before correction (after correction-before correction).

The HbA1c % before the correction with [Equation B1] and that after the correction were not equal to each other, and the difference therebetween increased in a hemoglobin concentration-dependent manner (FIG. 4).

Thus, it was confirmed that there was a fluctuation in absorbance at 884 nm dependent on the hemoglobin concentration.

Example 3

The correction of the fluctuation in absorbance at 884 nm dependent on the hemoglobin concentration was investigated.

1. Procedure

The hemoglobin concentration of each panel specimen measured at 884 nm used in Example 2 was defined as (x) and the change in absorbance of the panel specimen at 884 nm was defined as (y), and a correlation coefficient ($R^2$) and regression equation (y=ax−b) therebetween were determined.

2. Results

Figure 5:
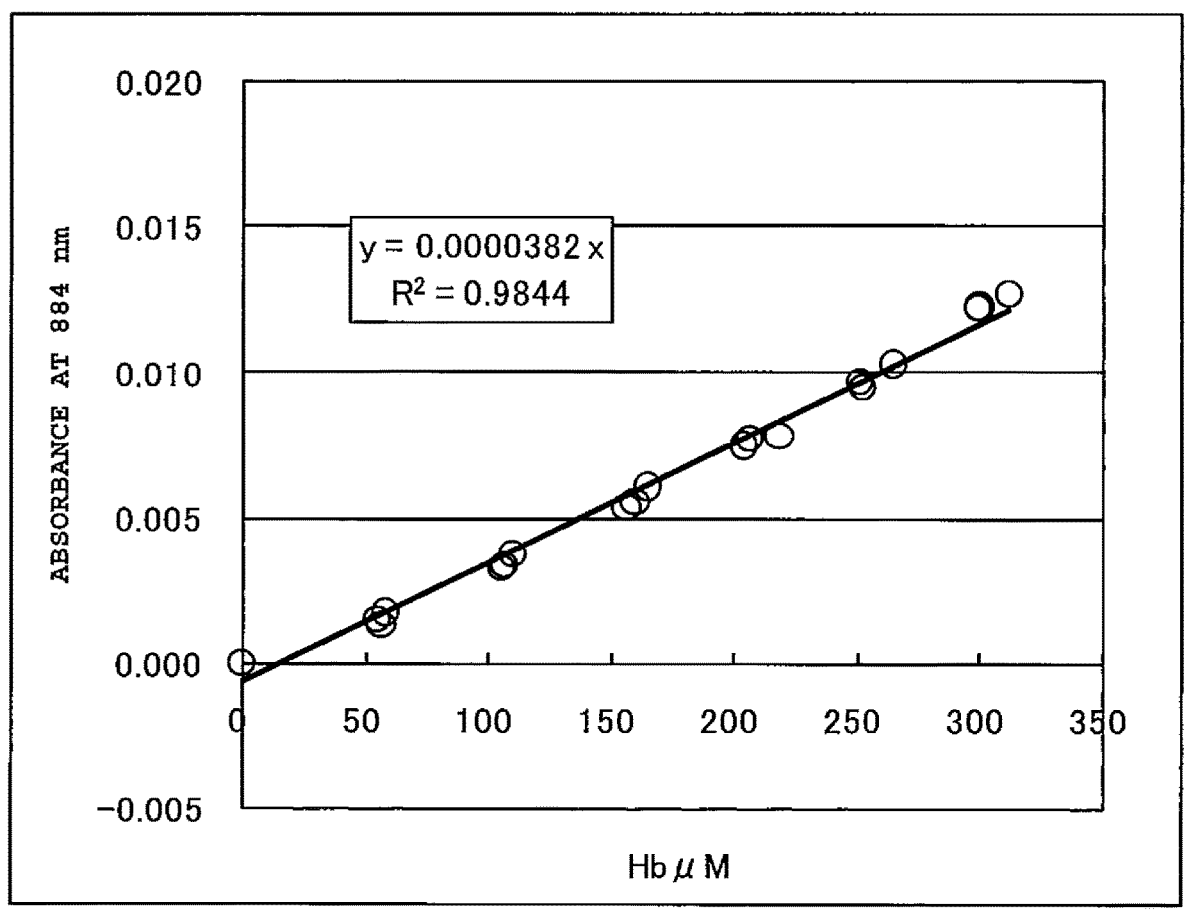
FIG. 5 is a graph for showing a relationship between a hemoglobin concentration and an absorbance change at the second wavelength (884 nm).

The correlation coefficient: $R^2$=0.9844 and the regression equation: y=$3.82*10^{-5}$x−0 [Equation C1] were obtained. It was confirmed again that there was an absorbance change at 884 nm dependent on the hemoglobin concentration (FIG. 5).

Example 4

The correction of the hemoglobin concentration measured value at 478 nm utilizing the absorbance change at 884 nm dependent on the hemoglobin concentration was investigated.

1. Procedure

The change in absorbance at 884 nm dependent on the hemoglobin concentration was determined by the regression equation [Equation C1] obtained in Example 3, and through the utilization thereof, [Equation D1] for determining a net hemoglobin concentration rise due to Intralipos (Otsuka Pharmaceutical Factory, Inc.) at 884 nm was derived. Then, the corrected value of the false increase in hemoglobin concentration value was calculated by an equation ([Equation E1]) utilizing [Equation D1]. On the basis of the foregoing, finally, [Equation F1] for determining a corrected hemoglobin concentration was derived.

2. Results

Change in absorbance at 884 nm dependent on hemoglobin concentration=hemoglobin concentration×3.82*10$^{-5}$  [Equation C1]

Net absorbance rise due to Intralipos at 884 nm=absorbance at 884 nm−(value obtained in [Equation C1])  [Equation D1]

Corrected value of false increase in hemoglobin concentration value=(value obtained in [Equation D1])*1,400  [Equation E1]

Corrected hemoglobin concentration=hemoglobin concentration calculated at 478 nm−(value obtained in [Equation E1])

=1.055*hemoglobin concentration−absorbance at 884 nm*1,400  [Equation F1]

Example 5

The validity of [Equation F1] was confirmed.
1. Materials
(1) Sample: The pooled whole blood was used.
(2) Measurement reagents and calibrator: The same measurement reagents and calibrator as those of Reference Example 1 were used.
(3) Lipid emulsions: Intralipid and Intralipos (Otsuka Pharmaceutical Factory, Inc.), and Interference Check A Plus chyle (Sysmex Corporation) were used.
2. Procedure
(1) Preparation of test samples: Test samples were prepared by adding each of the lipid emulsions to the pooled whole blood at final concentrations in Table 3a to Table 3c.
(2) Measurement of test samples: Through the use of an automated analyzer JCA-BM9130 (JEOL Ltd.), the test samples were subjected to measurement with the following measurement parameters, and HbA1c % was measured.
Parameters:
[HbA1c and Hb]
Analysis method: EPA
Calculation method: MSTD
Measurement wavelength (sub/main): HbA1c 805/658, Hb 805/478
Main DET.Pl-P.m-P.n: HbA1c 0-95-98, Hb 0-44-47
Sub DET.P.p-P.r: HbA1c 44-47, Hb 0-0
Reaction time: 10 min
At the time of blood cell measurement:
Diluted specimen amount (blood cell amount): 4.0 µL
Diluent amount (diluent): 110 µL
At the time of calibrator measurement
Diluted specimen amount (calibrator): 25 µL
Diluent amount (diluent): 15 µL
Reaction specimen amount (Sample amount): 6.4 µL
First reagent amount (R1): 60 µL, second reagent amount: 0 µL,
Third reagent amount (R2): 20 µL, fourth reagent amount: 0 µL
[884 nm]
Analysis method: EPA
Calculation method: ABS
Measurement wavelength (sub/main): Hb none/884 nm
FV=1
Main DET.Pl-P.m-P.n: Hb 0-44-47
Sub DET.P.p-P.r: Hb 0-0
Reaction time: 10 min
At the time of blood cell measurement:
Diluted specimen amount (blood cell amount): 4.0 µL
Diluent amount (diluent): 110 µL
At the time of calibrator measurement
Diluted specimen amount (calibrator): 25 µL
Diluent amount (diluent): 15 µL
Reaction specimen amount (Sample amount): 6.4 µL
First reagent amount (R1): 60 µL, second reagent amount: 0 µL,
Third reagent amount (R2): 20 µL, fourth reagent amount: 0 µL
*Physiological saline is used at the time of calibration at 884 nm.
Inter-Item Operation
[Corrected Hb]
Number of digits: 1, Qualitative judgment: None
X: 884 nm, Y: Hb Inter-item operational expression: $1.055*Y-1400*X \rightarrow$ [Equation F1]

[NGSP %]
Number of digits: 2, Qualitative judgment: None
X: HbA1c, Y=corrected Hb Inter-item operational expression: $X/Y*91.5+2.15$ 3. Results
The results of the addition of each of the lipid emulsions are shown in Table 3a to Table 3c. It was confirmed that, when correction was performed using [Equation F1], the falsely increased value of HbA1c % was able to be corrected irrespective of the kind of the lipid emulsion.

TABLE 3a

| Intralipid concentration (%) | HbA1c value before correction | Change ratio % | HbA1c value after correction | Change ratio % |
|---|---|---|---|---|
| 0.0 | 5.86 | 100.0 | 5.88 | 100.0 |
| 0.2 | 5.60 | 95.5 | 5.85 | 99.5 |
| 0.4 | 5.38 | 91.8 | 5.85 | 99.5 |
| 0.6 | 5.19 | 88.4 | 5.83 | 99.2 |
| 0.8 | 4.96 | 84.5 | 5.77 | 98.1 |
| 1.0 | 4.84 | 82.6 | 5.81 | 98.8 |

TABLE 3b

| Intralipid concentration (%) | HbA1c value before correction | Change ratio % | HbA1c value after correction | Change ratio % |
|---|---|---|---|---|
| 0.0 | 5.75 | 100.0 | 5.74 | 100.0 |
| 0.2 | 5.58 | 97.1 | 5.71 | 99.3 |
| 0.4 | 5.43 | 94.5 | 5.69 | 99.0 |
| 0.6 | 5.27 | 91.7 | 5.64 | 98.2 |
| 0.8 | 5.13 | 89.3 | 5.61 | 97.7 |
| 1.0 | 5.05 | 87.8 | 5.61 | 97.6 |

TABLE 3c

| Interference Check (FTU) | HbA1c value before correction | Change ratio % | HbA1c value after correction | Change ratio % |
|---|---|---|---|---|
| 0 | 5.86 | 100.0 | 5.88 | 100.0 |
| 600 | 5.82 | 99.4 | 5.89 | 100.2 |
| 1,200 | 5.80 | 99.0 | 5.93 | 100.8 |
| 1,800 | 5.75 | 98.2 | 5.92 | 100.7 |
| 2,400 | 5.72 | 97.7 | 5.93 | 100.8 |
| 3,000 | 5.69 | 97.1 | 5.96 | 101.3 |

Example 6

It was confirmed that [Equation F1] was also valid in the case of using a wavelength of 751 nm instead of a wavelength of 884 nm, and in HbA1c % measurement based on IFCC instead of NGSP %.

1. Materials
(1) Sample: The pooled whole blood was used.
(2) Measurement reagents and calibrator: The same measurement reagents and calibrator as those of Reference Example 1 were used.
(3) Lipid emulsion: Intralipid was used.
2. Procedure
(1) Preparation of test samples: Test samples were prepared by adding each lipid emulsion to the pooled whole blood at final concentrations in Table 4a and Table 4b.
(2) Measurement of test samples: Through the use of an automated analyzer JCA-BM9130 (JEOL Ltd.), the test samples were subjected to measurement with the measurement parameters of Example 5 some of which were changed, and HbA1c % was measured.

Only the parameters changed from Example 5 are described below.

Parameter of Example 5→parameter after change [884 nm]→[751 nm]

Measurement wavelength (sub/main): Hb none/884 nm→measurement wavelength (sub/main): Hb none/751 nm Inter-Item Operation 1
[Corrected Hb]
Number of digits: 1, Qualitative judgment: None
X: 751 nm, Y: Hb $1.053*Y-896*X\rightarrow$ [Equation $F1$] for 751 nm    Inter-item operational expression:

[NGSP %]
Number of digits: 2, Qualitative judgment: None
X: HbA1c, Y-corrected Hb $X/Y*91.5+2.15$    Inter-item operational expression:

Inter-Item Operation 2
[Corrected Hb]
Number of digits: 1, Qualitative judgment: None
X: 751 nm, Y: Hb $1.053*Y-896*X\rightarrow$ [Equation $F1$] for 751 nm    Inter-item operational expression:

[IFCC Value]
Number of digits: 2, Qualitative judgment: None
X: HbA1c, Y-corrected Hb $X/Y*1,000+0$    Inter-item operational expression:

3. Results

When corrected using [Equation F1] for 751 nm, the HbA1c % was able to be calculated without being influenced by Intralipid in both the case of NGSP % and the case of the IFCC value (Table 4a and Table 4b).

TABLE 4a

| 751 nm, NGSP % | | | | |
|---|---|---|---|---|
| Intralipid concentration (%) | HbA1c value before correction | Change ratio % | HbA1c value after correction | Change ratio % |
| 0.0 | 5.69 | 100.0 | 5.71 | 100.0 |
| 0.2 | 5.49 | 96.6 | 5.69 | 100.1 |
| 0.4 | 5.25 | 92.3 | 5.64 | 99.3 |
| 0.6 | 5.11 | 89.8 | 5.65 | 99.4 |
| 0.8 | 5.00 | 88.0 | 5.64 | 99.2 |
| 1.0 | 4.81 | 84.6 | 5.59 | 98.3 |

TABLE 4b

| 751 nm, IFCC value (mmol/mol) | | | | |
|---|---|---|---|---|
| Intralipid concentration (%) | HbA1c value before correction | Change ratio % | HbA1c value after correction | Change ratio % |
| 0.0 | 38.64 | 100.0 | 38.35 | 100.0 |
| 0.2 | 36.51 | 94.5 | 38.37 | 100.0 |
| 0.4 | 33.87 | 87.6 | 37.56 | 98.0 |
| 0.6 | 32.31 | 83.6 | 38.00 | 99.1 |
| 0.8 | 31.16 | 80.6 | 38.54 | 100.5 |
| 1.0 | 29.06 | 75.2 | 37.66 | 98.2 |

Example 7

The validity of [Equation F1] was confirmed using actual specimens.

1. Materials
(1) Sample: 350 cases of whole blood collected with EDTA (having a TG value in a standard range and having no visually observable turbidness) were used.
(2) Measurement reagents and calibrator: The same measurement reagents and calibrator as those of Reference Example 1 were used.
2. Procedure
(1) Measurement of samples: Through the use of an automated analyzer JCA-BM9130 (JEOL Ltd.), the test samples were subjected to measurement with the measurement parameters described in Example 5, and HbA1c % was measured through the correction of a 478 nm hemoglobin concentration using [Equation F1].
3. Results The HbA1c % before correction with [Equation F1] was defined as (x) and the HbA1c % after the correction was defined as (y), and a correlation therebetween was confirmed. As a result, the correlation coefficient: $R^2=0.9999$ and the regression equation: y=0.993x+0.0199 were obtained, and thus it was confirmed that the method of the present invention was usable even when an actual specimen was subjected to measurement (FIG. 6).

The invention claimed is:
1. A method of measuring a ratio of a hemoglobin A1c concentration to a hemoglobin concentration in a sample by an enzymatic method, comprising
   a) optically determining a hemoglobin concentration, by measuring the hemoglobin concentration at a first wavelength selected from 450 nm to 610 nm in the sample;
   b) optically measuring hemoglobin concentration and lipid particle concentration at second wavelength selected from 690 nm to 900 nm in the sample;
   c) correcting the hemoglobin concentration obtained optically at the first wave length using the lipid particle concentration information and hemoglobin concentra- tion information optically determined at second wavelength to provide a corrected hemoglobin concentration;
d) optically measuring hemoglobin A1c concentration,
e) calculating the HbA1c % by dividing the hemoglobin A1c concentration by the corrected hemoglobin concentration.

* * * * *